(12) United States Patent
Shanks et al.

(10) Patent No.: US 9,816,141 B2
(45) Date of Patent: Nov. 14, 2017

(54) HOST-ASSOCIATED DNA SEQUENCES, PRIMERS, AND PROBES FOR PCR-BASED IDENTIFICATION OF DOG FECAL POLLUTION SOURCES

(71) Applicant: U.S. ENVIRONMENTAL PROTECTION AGENCY, Washington, DC (US)

(72) Inventors: Orin C. Shanks, Cincinnati, OH (US); Hyatt C. Green, Cincinnati, OH (US)

(73) Assignee: U.S. Environmental Protection Agency, Washington, DC (US)

( * ) Notice: Subject to any disclaimer, the term of this patent is extended or adjusted under 35 U.S.C. 154(b) by 131 days.

(21) Appl. No.: 14/231,296

(22) Filed: Mar. 31, 2014

(65) Prior Publication Data

US 2015/0368695 A1 Dec. 24, 2015

(51) Int. Cl.
*C12Q 1/64* (2006.01)
*C12P 19/34* (2006.01)
*C12Q 1/68* (2006.01)

(52) U.S. Cl.
CPC .................................. *C12Q 1/689* (2013.01)

(58) Field of Classification Search
None
See application file for complete search history.

(56) References Cited

PUBLICATIONS

GenBank Accession No. FP929053, [publicly available Feb. 2015, retrived on-line http://www.ncbi.nlm.nih.gov/nuccore/fp929053].*
Kildare et al., "16S rRNA-based assays for quantitative detection of universal, human-, cow-, and dog-specific fecal Bacteriodales: A Bayesian approach," Water Research, 2007, vol. 41, pp. 3701-3715.*

* cited by examiner

*Primary Examiner* — Young J Kim
(74) *Attorney, Agent, or Firm* — Stein IP, LLC; Glenna Hendricks

(57) ABSTRACT

A method for detecting dog-fecal contamination in a sample, comprising assaying the sample using a nucleotide sequence based genetic assay which comprises contacting the sample with at least one nucleic acid molecule having the nucleic acid sequence shown in SEQ ID NO: 1, 2, 3, 4, 5, 6, 7, 8, 9, 10, or 11, the nucleic acid sequence being capable of binding to a nucleic acid sequence in the sample, and detecting binding of the nucleic acid molecule to the nucleic acid sequence in the sample, wherein a presence of binding is indicative of the presence of dog-fecal contamination in the sample; the nucleic acid molecules; and a kit comprising at least two of the above-described nucleic acid molecules.

5 Claims, 1 Drawing Sheet

Open reading frames identified from GFE. Color gradations signify the mean amino acid identity of each open reading frame to its top hit in the database.
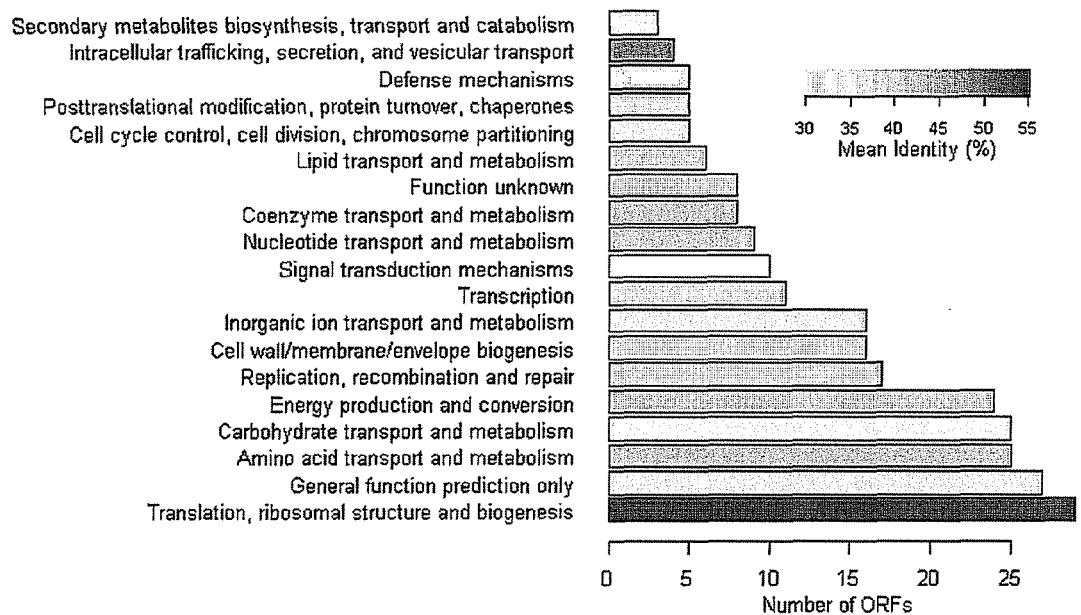

SEQUENCE LISTING

<160> NUMBER OF SEQ ID NOS: 11

<210> SEQ ID NO 1
<211> LENGTH: 582
<212> TYPE: DNA
<213> ORGANISM: bacteroides

<400> SEQUENCE: 1

```
ccctcgtaa tagttccgcc acgaagcaag atttcattgt tttcacctat tttagcctct      60
actcccggaa gcaaacgtcc cacggcaccg atgcggaaat catctttcca ttcacaagac     120
accgtagccg tactttctgt caatccatag ccggctacca tgttaatacc taccgaatga     180
acaaattcag ccacctttcc aggaatagcc gcaccggcag tcgggaaaaa gtttccgttg     240
tcaattccta tcgtcttttt caggaggctg taaatcgtcc gttcataaaa cttatatttc     300
atatgcaaca tcacgggagg agtcttacca ttcatcaggt aatcaatgtt atgcgcctta     360
cctacacgaa gggcatccaa catcagactc tttttcagcc ccgttgtttc gttaatcttt     420
tccagtacgc ccgcgtagac ttttcccag aaacggggca cactgcacat ggctgtaggg     480
cgaacctcct tgatggtttt aatatcctgc ggacggaggt taatgcagag caaacatcca     540
cggtctaaac aataatatga ccatgcccgc tcaaaaatgg ta                        582
```

<210> SEQ ID NO 2
<211> LENGTH: 355
<212> TYPE: DNA
<213> ORGANISM: bacteroides

<400> SEQUENCE: 2

```
ggcacgtaga gaatacgaag gtgagcgaga gaactgttgc caaggaactc ggcaaaatgg      60
ccccgtacgt tcgcaagaag gggcgctcga gagagccgca gtgaaaaggc ccaagcgact     120
gtttaactaa aacacagctc tatgcaaagc cgtaaggcga agtatatggg gtgacacctg     180
```

```
cccggtgctg aaggttaag gggatctgtt cgtcgcaaga caaagcagtg gtccgaagcc    240
ccagtgaacg gcggccgtaa ctataacggt cctaaggtag cgaaattcct tgtcgggtaa    300
gttccgaccc gcacgaaagg cgtaatgatt tgagcgctgt ctcgacaatc cagtg         355

<210> SEQ ID NO 3
<211> LENGTH: 550
<212> TYPE: DNA
<213> ORGANISM: bacteroides

<400> SEQUENCE: 3
tgaaataaga accagggaaa accttgagga aaaggagcta tcatagctga cgcatatcag     60
gaacactgat accgttcacg cccagtctgc gcttcctttg agcctgtagt ctcaaaggcg    120
ctcgacggga tcgcgtaaac ggtgtcaatg tcccggatat gctgttggca tgatagctct    180
ttgtgtatag gtgtgcagat ggagagtgtg tttgaataaa tcgaaaaagt ggaggcggat    240
tatggaagag tgtatgacaa agaggggagc caggctgatt gtgtatgtgc ctaaggagct    300
ggatcatcat tttgcagggg agatgacaga gatggtggat aaggagctta agaagggctg    360
tattaaacag cttgtctttg attttttctaa gacaacgttt atggacagtt ctggcattgg    420
gatgctaatg gggagaaagc ggctgttaag ctacagcgga ggaaccgtaa gtgctattca    480
tgttaatgac cggatttgc ggattatgca gccttcgggc atctggaaac acatggaaat    540
cagccaggaa                                                          550

<210> SEQ ID NO 4
<211> LENGTH: 416
<212> TYPE: DNA
<213> ORGANISM: bacteroides

<400> SEQUENCE: 4
tagtcctttt ctcccacggt catctgctct ttcatactgt ccataagaag ctgcttacat     60
tcctgtggat ccttaatatg cttttctgcc acctgctcct ttaaacgttc aataatagaa    120
gtggtagtat taattccaat gtcgcccata accaagattt cttcgatttc ctcatagaaa    180
tcctcgtcaa tactggaata accgctaaaa atagaatcaa ttcctgatac aatgttttct    240
ctggtttttg aaagacccctc taccaatctt ttaaaaaac ctttttctc ttttccctct    300 gccatagttc ctcctattta tctaaatcat gctcaatgag ttttacagac accagggtag    360
acacaccttt ttcctgcatg gtaattccat agagcctgtc tgctgctgtc atggtt       416

<210> SEQ ID NO 5
<211> LENGTH: 387
<212> TYPE: DNA
<213> ORGANISM: bacteroides

<400> SEQUENCE: 5
gtgctgacca aggaggtgag aagcagcact atcaaggcaa ttttaagaat cagcttgcgc     60
cgattgatta tgtcagatgg atgaagcata gtgactgtgt aacttaaatg ggtgttcaga    120
attcacacat ttgaacactt gcttgggtaa cttgaactt aaactcgatg cttaaaacgc    180
ctgaatggtg taaggtaaa gaacggctgc gggaatggca agcagtgagg agtcgaagcg    240
gtcgagcatg ccgccgtggc cggggagcac atggccgctg tctttaatac cagctgacgc    300
ttgaaaaggc tttcgaccag gtcgcccag gtgccgaata cgcataccgt caggcccaga    360
cccaaccagt ggagaagggg caaggtg                                       387
```

```
<210> SEQ ID NO 6
<211> LENGTH: 541
<212> TYPE: DNA
<213> ORGANISM: bacteroides

<400> SEQUENCE: 6
gacaatgccg acaggatagc cattggcata acgggattc gacactgaaa gacctacaac      60
gttcttgaac tttacgtaat aggtattagt ggattgaaaa acattgatac ccttgaggaa     120
attgagtcct ataaacagca gcacaagggc tactacagcg gtaagggcaa ttttaatttc    180
tttcttcatt gtatggtgaa tgaggttgta cttaaaggat tgggatgccc atgatatggg    240
gggagtggtg gcgcagaagc gtagggctta cttgcgttcg gctgcacggg cttgcttaat    300
ggttactttc tgaccattga gaaaggctac catataggca tcggggagtt tcttcaacac    360
tccgggcatg gcgcgatgtg cttcggcata gttcgtgaac gaaccgtgat agtatttata    420
gaggttgcct tctttcactc gctttacggt gagtcccttg aactgggggt cgcggggcga    480
aatttcgcga gttccggctg ccagttgaat gcagtaggtt acgacattgc cgaccacggt    540
a                                                                     541

<210> SEQ ID NO 7
<211> LENGTH: 376
<212> TYPE: DNA
<213> ORGANISM: bacteroides

<400> SEQUENCE: 7
cggtgagctg attggtacag gatttgaccg aaactatgaa ggtcttaccg gagatatcgc     60
ctacaatccg cagctacagc gtgctgcttg tgtagacatc cgctacacat tgtttatcat    120
tgataaattc gcaggtgcac gccatctcat cgatgaaatg acaatcatcc gataaggttg    180
attttaccat aaaaaaaga catcctacct gattacccga cataagtctg gggtttatca    240
aaagtaggat gtcttttttt atactatcct gtaaaaaaga aaagattat hgcttaatgc    300 ttgaatcgta tgacgcacac gttctgcagt agttacggga tatacatatt catcttggtc    360
tgaactgccc agggta                                                    376

<210> SEQ ID NO 8
<211> LENGTH: 709
<212> TYPE: DNA
<213> ORGANISM: bacteroides

<400> SEQUENCE: 8
tatctatccg ccataaagat gcatttggcg caggaggaag taccagcggt ggtgtagata     60
tacgcccttt cccaaacaac tgggagatga aaagcaact tggtgaggaa aaggagaatc    120
aaacccgctg ggacaatcat acagtaatga ctcaacttga caaatcaat ccgggtgatt    180 tggctttaat catagattgc ggttcagagg atttctttct cgaagtaaac gagcagctgc    240
ataaggttct gagtgacaaa ggtattccgc atgacttcat catccgcccg ggagtacacg    300
acgggaaata ctggaataac tcgattgatt accaatggat gttttttcaag aagttcttcg    360 atggataccg caataatcaa gacatacgcc cgtaggtaaa ggcatctctc cccaaccaag    420
gtgccgataa agggatatac agcttaaata cataggtaaa cttgccaaga agaaggtatt    480
gattatttca aggcttttg taaatttgca attatatact cagaaaaaga acgataatat    540
ggaaataacc agtgctgaat ttgtagtaag taactcgcgt gccgacatgt gcccggacac    600
ccaccttccc gaacatgcct ttatcggacg ctcgaacgta ggagaatcca gcttaatcaa    660
```

```
tatgctgacc aatcactcca atttggccat gacctcctca accccggta        709

<210> SEQ ID NO 9
<211> LENGTH: 285
<212> TYPE: DNA
<213> ORGANISM: bacteroides

<400> SEQUENCE: 9
cacggtaaaa aacggactga ctcccttcgc ttcactgatt tcagcaagtg gaatatcatg    60
tgtaataata gaagggaaga aagcttcgcc taccccgtaa gaaagaaaac ctgaaaacag   120
cgttgctcca taagccaaca aagcggttac tgccaacatc tttccggctc ctttacctat   180
atcggcaatg gctggggtaa ctaatccgac tataatcagc ggaatgataa aattaaggaa   240
ctgactgaac aacccgttga aggtgacaaa aaggcgtacc cggtg                   285

<210> SEQ ID NO 10
<211> LENGTH: 576
<212> TYPE: DNA
<213> ORGANISM: bacteroides

<400> SEQUENCE: 10
ttgagcttct tccagttaga cgaccctgtg ctttgtcaga ttcgtgatga aatcttgaat    60
ttggatgtga ataatctgac tcctctggag gcactgaata agttgaatga tattaagcgg   120
attgtaaggg gaaagtagac ttataaatca taaacttaaa aacgaaagcc ctatgaaaac   180
aatgaagtta ggacttcttc ctcccattct tattacgata gttttaggta ttttttgccgg   240 gatggtttca ccagctttcc cggtacgcct ttttgtcacc ttcaacgggt tgttcagtca   300
gttccttaat tttatcattc cgctgattat agtcggatta gttaccccag ccattgccga   360
tataggtaaa ggagccggaa agatgttggc agtaaccgct ttgttggctt atggagcaac   420
gctgttttca ggttttcttt cttacggggt aggcgaagct ttcttcccctt ctattattac   480 acatgatatt ccacttgctg aaatcagtga agcgaaggga gtcagtccgt tttttaccgt   540
gactattcct gagccctga atgtgataac atggca                              576

<210> SEQ ID NO 11
<211> LENGTH: 392
<212> TYPE: DNA
<213> ORGANISM: bacteroides

<400> SEQUENCE: 11
gaacgaccct tcgcgtccgt gtcataaaac ctacaccatc gacatggacc gtcactcgta    60
cgatggccag caatggactt acctgaacct gccgatggag gaaatcaagc agatggccat   120
tgcctcgatt aaggactcaa cgatgatgta ctactcatgc gacgtgggca aattcctgaa   180
cggcaaaacg ggtattcttt cgttgcagaa ctacgactac gagtcgcttt tcggcaccaa   240
cttccccatg acgaaggctg aacgcatcag caccttttgca tcggcgtcga gccatgccat   300
gacgctgatg gccgtagacc tcgacgccaa cggcaaaccg acgaagtgga tggttgaaaa   360
ctcttggggt gctacttcgg gccacaacgg ta                                 392
```

HOST-ASSOCIATED DNA SEQUENCES, PRIMERS, AND PROBES FOR PCR-BASED IDENTIFICATION OF DOG FECAL POLLUTION SOURCES

BACKGROUND OF THE INVENTION

Current regulatory methods used to assess microbial water quality rely on measuring the levels of culturable fecal indicator bacteria such as Enterococci and other fecal coliforms. However, the plate culture approach cannot discriminate among different specific bacterial strains or animal sources of fecal contamination.

Many studies have reported on the development of MST methods designed to target chemical indicators such as pharmaceuticals or the cultivation fecal bacteria isolated from particular animal sources. However, strategies that target genetic material isolated from fecal bacteria are the more widely reported. For example, ribotyping and rep-PCR DNA fingerprint techniques targeting *E. coli* isolates have been applied to discriminate among different animal fecal sources. However, the successful application of these genotypic methods depends on the development of large fingerprint databases of indicator bacterial isolates, primarily *E. coli*. Moreover, the use of *E. coli* for fecal source identification has been recently criticized in light of the abundance of secondary habitat populations that are capable of adapting to conditions outside of the animal gut and, as a result, contribute to the levels of fecal indicator bacteria in water.

Recently, Field and coworkers used library-independent methods based on ribosomal 16S rRNA gene sequences of *Bacteroides*-like bacteria to discriminate between human and ruminant feces. These *Bacteroides* markers have been used to identify non-point sources of fecal pollution in coastal and inland waters. However, these approaches often cannot not discriminate between fecal pollution sources at a species levels. For example, these methods can only discriminate between ruminant and non-ruminant animal sources due to the lack of genetic variation between *Bacteroides* 16S rRNA gene sequences originating from closely related animal species such as cows, sheep, deer, and other ruminants. Alternative MST methods capable of species level discrimination may prove more useful for fecal pollution characterization in recreational waters.

Functional genes involved in host-microbial interactions may represent a good pool of targets for host-specific assays. Some of these functional genes are hypothesized to be microbial surface proteins, while others may be associated with cellular processes and metabolism. However, a limited number of studies have used genes involved in host-microbial interactions as potential fecal community markers. This is probably due to the small number of microbial genes known to be involved in host-microbial interactions and the limited sequence information for these genes.

There is a demand for accurate microbial source tracking (MST) methods, because of language in the U.S. Clean Water Act regarding total maximum daily loads (TMDLs) and protection of supplies of drinking water. Current PCR-based MST approaches focus on various specific known DNA sequences, mostly targeting 16S rRNA (rDNA) genes, once thought to be source specific. However, validation studies are constantly uncovering exceptions and limitations with existing MST technologies. A significant part of the problem with existing 16S rRNA gene targeting MST methods stemmed from the inability to target microorganism DNA sequences encoding for proteins directly involved in host-microbe interactions, which are expected to contain high levels of genetic variation related to survival within different animal hosts.

Many specific approaches have previously attempted to determine sources of fecal contamination in the environment. One of the most widely used techniques is a PCR-based method that identifies ruminant fecal pollution by targeting bacterial 16S rRNA gene sequences from *Bacteroides* (Bernard and Field, AEM 66:4571-4574, 2000). The present inventors have conducted ongoing validation studies of these methods, and have discovered that previously described proposed ruminant specific markers can amplify rRNA gene sequences from non-ruminant fecal samples collected from geographic regions outside the original watersheds sampled. By definition, these previously described PCR target regions identify cow, deer, elk, goat, sheep, and other ruminants and pseudo-ruminants. This approach is therefore less useful in watersheds impacted by more than one ruminant animal source.

While advances in DNA sequencing and computational biology allow scientists to compare entire microbial genomes and discern microorganism-specific genetic information, sequencing of multiple closely related bacterial genomes so far remains prohibitively expensive and impractical for all but a very small number of laboratories. The entire genome content of more than 238 bacterial species have so far been defined through whole genome sequencing of representative type strains, and the number of genome sequences continues to increase. While significant differences in the genome content of different species are well-established, comparisons between genomes of closely related bacteria are equally important. These comparisons can provide species and strain-specific genetic information, define metabolic pathways and virulence factors, and provide insights into capacities for host-interactions, cell-to-cell signaling, stress response, and other essential microbial cellular functions.

Current DNA-based technologies potentially capable of identifying source, species, and strain-specific genetic markers include Suppressive Subtractive Hybridization (SSH) (Diatchenko et al., PNAS 93:6025-6030, 1996). This technique uses intentionally biased PCR amplification of nucleic acid pools to enrich for unique segments of restricted DNA relative to non-target DNA. SSH has been successfully applied in several pair-wise comparative genome studies (e.g., Nguyen et al., 2004, AEM 71 2564-2575), but only on one "metagenomic" or total microbial community DNA study (Galbraith et al., 2004; Environmental Microbiology: 928-937). SSH is a negative selection process that relies on unequal PCR amplification to amplify all dissimilar sequences from two nucleic acid pools. This is achieved by adding different self-complementary flanking regions to each of two fragment pools, and inhibition of amplification of only those duplexes that re-anneal relative to new heteroduplexes that form following denaturation and reassociation of the mixture.

One of the limitations of currently available MST methods arises from the inability of previously described techniques to target microorganism DNA sequences potentially encoding proteins directly involved in host-microbe interactions. These regions, unlike rRNA gene operons, are expected to retain high levels of genetic variation in microbes found in association with different animal hosts.

U.S. Pat. Nos. 7,572,584; 8,058,000, and 8,574,839 disclose positive DNA selection approaches designated Genome Fragment Enrichment (GFE) technique, and its efficient use in detecting fecal pollution from particular animal species and individual sources in environmental samples.

It is an object of the present invention to overcome the described deficiencies in the prior art.

SUMMARY OF THE INVENTION

An embodiment of the disclosure comprises a method for detecting dog-fecal contamination in a sample, comprising assaying the sample using a nucleotide sequence based genetic assay which comprises contacting the sample with at least one nucleic acid molecule having the nucleic acid sequence shown in SEQ ID NO: 1, 2, 3, 4, 5, 6, 7, 8, 9, 10, or 11, the nucleic acid sequence being capable of binding to a nucleic acid sequence in the sample, and detecting binding of the nucleic acid molecule to the nucleic acid sequence in the sample, wherein a presence of binding is indicative of the presence of dog-fecal contamination in the sample.

An additional embodiment of the disclosure comprises the nucleic acid molecules having the nucleic acid sequences shown in SEQ ID NO: 1, 2, 3, 4, 5, 6, 7, 8, 9, 10, 11, or full complements thereof and capable of binding to a nucleic acid sequence in a sample containing fecal contamination.

A further embodiment of the disclosure relates to a kit comprising at least two of the above-described nucleic acid molecules.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1 shows open reading frames identified from GFE.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the FIGURES.

There are approximately 78.2 million owned dogs in the United States. It is estimated that 39% of all households in the United States own at least one dog. Because these animals cohabitate with humans, it has been extremely difficult to develop technologies that can discriminate between human and dog fecal pollution. Dogs and their owners are known to frequent beaches, lakes, and parks situated near recreational water ways or storm sewage drains that discharge into local waters. Studies have shown that dog feces contains very high concentrations of enterocococi, a general fecal indicator bacteria recommend by the U.S. EPA for National Ambient Water Quality Criteria designed to keep the public safe from exposure to fecal pollution. Thus, it is impossible for a water manager to determine if high levels of general fecal indicators (i.e., enterococci) at a local beach where both human and dogs are present originates from humans, humans and dogs, or just dogs.

The host-associated technologies described here have several advantages over prior methods. First, our methods can differentiate between the select animal and other animal fecal pollution sources. Second, our methods target non-ribosomal genes predicted to be involved in host-associated metabolic activities. These genetic targets have never been used to develop host-associated fecal technologies for these animal groups. Third, our methods will work with populations from across the United States, where as it is currently unknown how effective prior art technologies are in this regard.

EXAMPLE

Sample Collection.

Fecal samples were collected over a wide geographic range. During transit from the field to the laboratory, samples were stored on ice and upon arrival, stored at −80° C. Sewage influent samples were also collected over a wide geographic range. Urban stormwater runoff samples were collected from a local rain garden over a 27 hour storm event. Water samples were retrieved within eight hours from the end of sampling and split for culture analysis of total coliforms and *E. coli* (MPN method, IDEXX Labs, Westbrook, Me.) and qPCR analysis. Automated sampler blanks were made by rinsing unused sample bottles with 50 ml distilled water prior to filtration. Filtrates from 50 ml of each stormwater sample were collected on 0.4 µM polycarbonate filters (Whatman, GE Healthcare Life Sciences, Piscataway, N.J.) and stored at −80° C. overnight prior to DNA extraction. A filter blank was performed in manner described above except that 50 ml of molecular grade water was used instead of stormwater.

Total DNA Extraction and Quantification.

Both fecal and stormwater samples were extracted using the GeneRite DNA-EZ kit #DNA-EZ RW02 [Shanks, O. C., et al., *Competitive Metagenomic DNA Hybridization Identifies Host-Specific Microbial Genetic Markers in Cow Fecal Samples*. Appl. Environ. Microbiol., 2006. 72(6): p. 4054-4060], North Brunswick, N.J.] according to the manufacturer's instructions with modifications. For fecal samples, about 0.5 g fecal sample was added to 1 ml GITC buffer and vortexed to make fecal slurries. Four hundred microliters elution buffer and 700 µl fecal slurry were added to the bead mill tube and agitated at 6 m/s for 40 sec. After centrifuging bead mill tubes for one minute at 14,000 g, 500 µl supernatant was combined with 1000 µl binding buffer and vortexed. This mixture was then added to the DNA binding column and washed twice with wash buffer. DNA was eluted with 100 µl warm elution buffer and stored at −20° C. until further analysis. DNA was extracted from water sample filtrates in the same manner except that 500 µl GeneRite lysis buffer and 12 ng Salmon sperm DNA was added to the tube with the filter instead of GITC and no elution buffer was added to the bead mill tube resulting in only 500 µl lysate being added to the bead tube before agitating. One or two extraction blanks were included with every extraction batch by adding 700 µl molecular grade water to the bead tube instead of fecal slurry or lysate for a total of 22 extraction blanks. Total DNA concentrations for each sample were estimated with PicoGreen (Life Technologies) following the manufacturers protocol on a SpectraMax® Paradigm® plate reader (Molecular Devices, Sunnyvale, Calif.).

Genome Fragment Enrichment and Enriched Sequence Annotation.

GFE was performed as previously described [Shanks, O. C., et al., *Identification of bacterial DNA markers for the*

*detection of human fecal pollution in water.* Appl Environ Microbiol, 2007. 73(8): p. 2416-22; Shanks, O. C., J. W. Santo Domingo, and J. E. Graham, *Use of competitive DNA hybridization to identify differences in the genomes of bacteria.* J Microbiol Methods, 2006. 66(2): p. 321-30; Shanks, O. C., et al., *Competitive Metagenomic DNA Hybridization Identifies Host-Specific Microbial Genetic Markers in Cow Fecal Samples.* Appl. Environ. Microbiol., 2006. 72(6): p. 4054-4060] using dog fecal total DNA as the target and swine fecal DNA as the blocker. Fragments were ligated into pCR4-TOPO plasmids and transformed into One Shot Top10 cells (Life Technologies, Carlsbad, Calif.). Amplicon Sanger sequencing was performed on an ABI PRISM 3730XL DNA Analyzer. Low quality sequence regions were removed by visual inspection. In some cases this resulted in discarding entire sequence fragments.

Predictions of possible gene function and taxonomic association were obtained through the RAMMCAP [Li, W., *Analysis and comparison of very large metagenomes with fast clustering and functional annotation.* BMC Bioinformatics, 2009. 10: p. 359] via CAMERA [Sun, S., et al., *Community cyberinfrastructure for Advanced Microbial Ecology Research and Analysis: the CAMERA resource.* Nucleic Acids Res, 2011. 39(Database issue): p. D546-51] and MG-RAST [Meyer, F., et al., *The metagenomics RAST server—a public resource for the automatic phylogenetic and functional analysis of metagenomes.* BMC Bioinformatics, 2008. 9: p. 386] pipelines, respectively. Identification of unique sequences was performed with CD-HIT using a 90% identity threshold [Li, W. and A. Godzik, *Cd-hit: a fast program for clustering and comparing large sets of protein or nucleotide sequences.* Bioinformatics, 2006. 22(13): p. 1658-9]. Identification of open reading frames (ORFs) was performed with Metagene [Noguchi, H., J. Park, and T. Takagi, *MetaGene: prokaryotic gene finding from environmental genome shotgun sequences.* Nucleic Acids Res, 2006. 34(19): p. 5623-30]. Marker selection by function was based on annotations using the Clusters of Orthologous Groups (COG) database [Kristensen, D. M., et al., *A low-polynomial algorithm for assembling clusters of orthologous groups from intergenomic symmetric best matches.* Bioinformatics, 2010. 26(12): p. 1481-7; Tatusov, R. L., E. V. Koonin, and D. J. Lipman, *A genomic perspective on protein families.* Science, 1997. 278(5338): p. 631-7]. Since database content has changed significantly since the time of initial fragment isolation and sequencing, more recent and perhaps more accurate annotations of selected marker fragments using BLASTx and the NCBI Protein Reference Sequence database were conducted.

Selection of Candidate Sequences for PCR-Based Assay Development.

Sequences without statistically significant homology to sequences stored in sequence databases or the order Bacteroidales (e-value≥0.001) were not selected for marker development. Thirty-eight sequences distributed across all functional categories were selected for marker development including sequences with hypothetical functions only. Forty-six sequences attributed to Bacteroidales bacteria were randomly selected for primer design. In some cases, a single sequence was used to design more than one primer set. In all, 84 sequences were used to design 92 primer sets for further testing.

Oligonucleotide Design and Preparation.

Unique regions in putative marker sequences were selected for primer design by comparison with existing sequence information. Primer-BLAST was used to perform in silico tests to predict target specificity and melting temperature (60±2° C.). For each TagMan® qPCR assay, two probes were designed to target short sequence regions with high amino acid conservation. The probe which resulted in the highest sigmoidal efficiency across a canine fecal DNA dilution series was selected for further testing.

Standard Curve Generation.

To generate standard curves, decimal dilutions of a custom plasmid ($5 \times 10^{-4}$ to 5 copies/µl) that contained target sequence regions of all canine-associated assays (IDT, San Jose, Calif.) were used as template for each assay. Similar plasmid constructs were used to generate standard curves for HF183/BacR287 and GenBac3. Data from six separately run standard curves (duplicate reactions at each concentration) were compiled by pooling data from each run for each assay using simple linear regression.

PCR and qPCR.

Takara Ex Taq® Hot Start Version PCR reagents (Clontech Labs, Mountain View, Calif., USA), 200 nM each primer, 4.0 ng BSA, 2 µl template DNA, and molecular grade water were used for all endpoint PCR reactions. PCR products were visualized using 2% agarose gels with lithium borate buffer and 1× GelStar™ (Lonza, Allendale, N.J., USA). Unless otherwise stated, all endpoint PCR reactions were run for 35 cycles on a Tetrad 2 thermal cycler (Bio-Rad Laboratories, Hercules, Calif.). Twenty five microliter qPCR reactions consisted of 1× TaqMan® Environmental Master Mix (Life Technologies), 5.0 ng BSA, 1400 nM each primer, 100 nM probe (TaqMan® reactions only), 0.1×SYBR® Green 1 Dye (SYBR® Green reactions only; Life Technologies), 2 µl template DNA, and molecular grade water. All qPCR reactions were run for 40 cycles on a StepOne Plus instrument (Life Technologies). Four reaction replicates were run for each DNA sample. Reaction fluorescence from cycles eight to thirteen was used to establish baseline fluorescence and a fluorescence threshold of 0.03 was used for all canine qPCR assays. A minimum of two no template control reactions were included with each qPCR instrument run. TaqMan® qPCR assays HF183/BacR287 (in press), GenBac3, and Sketa22 were used as previously described.

Assay Selection.

In order to determine which assays have diagnostic fecal source identification potential, the 92 primer sets were initially tested with endpoint PCR on two fecal DNA composites. One, a canine fecal DNA composite (0.05 ng total DNA/µl) consisting of equal DNA masses from 20 canine individuals (10 each from Florida and Wyoming populations) were used to determine the presence or absence of markers within the target host group. Two, a DNA composite consisting of human, cattle, and goose fecal DNA (0.625 ng total DNA/µl, equal DNA mass per source species) was used to determine the presence of markers in likely sources of contaminants other than dogs. For the initial assay screening phase only, the number of endpoint PCR amplification cycles was decreased from 35 to 30 when using canine fecal DNA as template to select for markers with high abundance in dogs. Assays were discarded from further analysis if any of the following conditions were met: 1) an amplification product of the expected size was absent when using canine fecal DNA as template, 2) amplification products of any size were produced when the non-canine fecal DNA composite was used as template, or 3) amplification byproducts, such as primer dimerization molecules or other spurious PCR products noticeably different in size from the expected PCR product, were produced when using either fecal DNA composite as template. Primer sets that met these criteria were used for more rigorous endpoint PCR testing against fecal DNA extracts listed in Table 1.

For this second phase of testing, non-canine fecal DNA composites consisting of 0.5 ng DNA µl$^{-1}$ individual$^{-1}$ were used to characterize marker distributions outside canine populations. Individual canine DNA extracts (0.5 ng/µl) were used to investigate the marker distributions within canine populations. Assays that had the highest estimates of specificity and maintained high levels of sensitivity after this second phase of screening were used as the basis for three qPCR assays.

SYBR® qPCR assays were created by incorporating each forward and reverse primer into a SYBR® Green qPCR chemistry platform without any modifications. The same was done for TaqMan® qPCR assays, but with the addition of an internal probe and exclusion of SYBR® Green Dye. qPCR assays were then optimized for maximum specificity and efficiency (sigmoidal) by testing a range of primer (200-4000 nM) and probe (40-180 nM) reaction concentrations. At least two probes were tested for each TaqMan® qPCR assay and the probe that resulted in the highest sigmoidal efficiency while maintaining specificity was chosen for further study. Amplification Interference and DNA Recovery Controls. Kinetic outlier detection (KOD) was used to check for amplification interference in all samples tested [Green, H. C. and K. G. Field, *Sensitive detection of sample interference in environmental qPCR*. Water Res, 2012. 46(10): p. 3251-60; Tichopad, A., et al., *Quality control for quantitative PCR based on amplification compatibility test*. Methods, 2010. 50(4): p. 308-12]. Briefly, genomic (Sketa22 only, 1-10$^{-5}$ ng/rxn) or plasmid (all other assays, 10$^5$-10$^{-1}$ copies/rxn) DNA dilutions were used to generate a KOD reference data set. Then, reference and experimental fluorescence data were fit to a seven-parameter sigmoidal model and the linear relationship between fractional cycle values at first and second derivative maxima were used to estimate normal and outlier amplification profiles. Reactions with $T_{norm}$ values less than the 99.9% quantile using $\chi^2$ distribution with one degree of freedom (−15.13) were considered significantly inhibited, but samples were not excluded from analysis unless all replicate reactions for a particular sample exceeded this threshold. All samples that amplified fit sigmoidal models with $R^2$>0.999. The two samples containing levels of inhibitors were considered positive but non-quantifiable, and were excluded only from quantitative analysis. For stormwater samples, both DNA recovery and amplification interference was estimated with the Sketa22 assay similar to methods described previously [Green, supra]. Briefly, 12 µg Salmon sperm DNA was added to the sample before DNA extraction instead of *E. coli* AF504 GFP cells. Sketa22 amplification profiles were first checked for amplification inhibition using the methods described above. Amplification profiles that passed amplification criteria were then used to estimate total DNA recovery as a percentage of the total spiked salmon sperm DNA.

Data Analysis and Performance Parameter Definition.

In R, package qpcR [Ritz, C. and A. Spiess, *qpcR: an R package for sigmoidal model selection in quantitative real-time polymerase chain reaction analysis*. Bioinformatics, 2008. 24: p. 1549-1551] was used for sigmoidal model fitting (functions modlist and perbatch) and package epitools [Liu, W. and D. A. Saint, *Validation of a quantitative method for real time PCR kinetics*. Biochemical and Biophysical Research Communications, 2002. 294(2): p. 347-353] was used to estimate binomial confidence intervals (function binom.exact). Marker prevalence was defined as the proportion of individuals that contained a marker. Specificity was defined as the proportion of non-canine samples testing negative for a canine marker. Sensitivity was defined as the proportion of canine samples testing positive for a canine marker. Sigmoidal efficiency, defined as the cycle specific efficiency ($E_n$) at the second derivative of the fitted amplification curve where $E_n=F_n/(F_{n-1})$ and $F_n$ and $F_{n-1}$ are the cycle specific fluorescence values at cycles n and n-1 [Liu, W. and D. A. Saint, *Validation of a quantitative method for real time PCR kinetics*. Biochemical and Biophysical Research Communications, 2002. 294(2): p. 347-353], was used to estimate amplification efficiency during assay optimization. Amplification efficiency estimates from calibration curves were obtained using the equation $E=10^{(1/-slope)}/2$. Limit of quantification (LOQ) was defined as the lowest concentration of plasmid standard whose resulting mean Cq value fell within a linearity ($R^2$>0.97). $Cq_{LOQ}$ was defined as the mean Cq value at the LOQ. For TaqMan® reactions, the assay LOQ (10 plasmid copies/reaction, lowest concentration tested) was also considered the assay limit of detection (LOD). However, since SYBR® Green melt curve analysis could reliably distinguish smaller amounts of amplified target template from non-specific amplification products, any set of replicate reactions whose melt curves revealed the intended PCR product, regardless of their Cq values or the presence of side-product melt temperature ($T_m$) peaks, was considered to be in the detectable range. Thus, SYBR® reactions were interpreted as non-detections when a target $T_m$ peak was absent in any of the replicate reactions. SYBR® reactions with the single intended $T_m$ peak and Cq values within the LOQ were interpreted as quantifiable. Experimental $T_m$ peaks within four standard deviations of the anticipated assay specific $T_m$ peak (estimated using reference plasmids) were classified as target $T_m$ peaks. Loads were estimated by first assuming that samples whose marker concentrations were below LOQ contained one marker copy. Loads of each sample were then averaged to obtain mean loads.

Annotation of Putative Canine-Associated DNA Sequences:

Enriched sequence fragments were highly diverse in sequence composition and annotated function. Overall, sequences had very low similarity to reference database sequences, which made functional annotations difficult in some cases. Only 59.8%, 33.3%, and 41.4% of the 747 putative open reading frames (ORFs) had significant matches when searched against TIGRFAM, PFAM, and COG databases as of Nov. 11, 2011 (e-value 0.001), respectively. ORFs predicted to encode for genes involved in translation, ribosomal structure, and biogenesis were the most abundant (FIG. 1). Color gradations signify the mean amino acid identities of each open reading frame to its top hit in the database within each functional group.

Development of Canine-Associated Endpoint PCR Assays:

Eighty-four sequences were selected for the development of 92 endpoint PCR assays based on functional and taxonomic annotations. Each endpoint PCR assay was tested using canine and mixed source fecal DNA composites. Twelve endpoint PCR assays (Table 1) were deemed eligible for sensitivity and specificity testing because they amplified a single expected PCR product from a canine fecal DNA composite and did not amplify PCR products from a non-canine fecal DNA preparation.

TABLE 1

Fragments annotations for which endpoint PCR assays were developed were used to query the NCBI Protein Reference Sequence Database using BLASTx.

| Assay | Length | Taxonomy | Function | Accession | % Query Coverage | % Sequence ID (AA) | E-value |
|---|---|---|---|---|---|---|---|
| DG2 DG3[α] | 676 | Bacteroides plebeius | long-chain fatty acid-CoA ligase | WP_007559956.1 | 98 | 89 | 4.00E−12 |
| DG5 | 355 | Caldanaerobacter subterraneus | hypothetical protein | WP_009610708.1 | 59 | 92 | 1.00E−22 |
| DG29 | 550 | Lachnospiraceae | anti-sigma F factor antagonist | WP_003022855.1 | 56 | 77 | 3.00E−49 |
| DG37 | 416 | Lachnospiraceae | cell division protein FtsY | WP_003021240.1 | 71 | 89 | 4.00E−43 |
| DG39 | 388 | Alloprevotella tannerae | phosphatidate cytidylyltransferase | WP_006254289.1 | 45 | 90 | 5.00E−29 |
| DG46 | 541 | Prevotella sp. oral taxon 473 | hypothetical protein | WP_009436627.1 | 33 | 74 | 1.00E−16 |
| DG68 | 377 | Bacteroides dorei | hypothetical protein | WP_007837027.1 | 44 | 95 | 2.00E−29 |
| DG72 | 709 | Bacteroides coprocola | hypothetical protein (esterase) | WP_007571683.1 | 52 | 77 | 8.00E−63 |
| DG74 | 285 | Bacteroides | sodium:proton antiporter | WP_007562866.1 | 97 | 86 | 2.00E−45 |
| DG75 | 576 | plebeius | | | 69 | 83 | 1.00E−64 |
| DG80 | 392 | Prevotella sp. oral taxon 473 | putative aminopeptidase E | WP_009436828.1 | 99 | 77 | 4.00E−66 |

[α]Endpoint, SYBR® Green qPCR, and TaqMan® qPCR assays designed for assays in bold. For all other assays only endpoint versions were designed.

Secondary screening using 199 reference fecal DNA extracts demonstrated that all 12 assays exhibited high levels of specificity ranging from 89% to 100% and sensitivity from 73% to 95% (Table 2).

TABLE 2

Estimates of specificity and sensitivity for 12 canine-associated endpoint-PCR assays.

| | Specificity | | | | Sensitivity | | | |
|---|---|---|---|---|---|---|---|---|
| Assay | Num. Pos, n = (133) | Estimate | LCI[α] | UCI | Num. Pos, n = (66) | Estimate | LCI | UCI |
| DG2 | 2 | 0.98 | 0.95 | 1.00 | 52 | 0.79 | 0.67 | 0.88 |
| DG3 | 0 | 1.00 | 0.97 | 1.00 | 51 | 0.77 | 0.65 | 0.87 |
| DG5 | 5 | 0.96 | 0.91 | 0.99 | 51 | 0.77 | 0.65 | 0.87 |
| DG29 | 15 | 0.89 | 0.82 | 0.94 | 63 | 0.95 | 0.87 | 0.99 |
| DG37 | 0 | 1.00 | 0.97 | 1.00 | 56 | 0.85 | 0.74 | 0.92 |
| DG39 | 8 | 0.94 | 0.88 | 0.97 | 48 | 0.73 | 0.6 | 0.83 |
| DG46 | 3 | 0.98 | 0.94 | 1.00 | 48 | 0.73 | 0.6 | 0.83 |
| DG68 | 0 | 1.00 | 0.97 | 1.00 | 51 | 0.77 | 0.65 | 0.87 |
| DG72 | 0 | 1.00 | 0.97 | 1.00 | 50 | 0.76 | 0.64 | 0.85 |
| DG74 | 3 | 0.98 | 0.94 | 1.00 | 52 | 0.79 | 0.67 | 0.88 |
| DG75 | 1 | 0.99 | 0.96 | 1.00 | 52 | 0.79 | 0.67 | 0.88 |
| DG80 | 7 | 0.95 | 0.89 | 0.98 | 48 | 0.73 | 0.6 | 0.83 |

[α]LCI and UCI are 95% lower and upper confidence intervals based on a binomial distribution, respectively.

Development of Canine-Associated qPCR Assays.

The top performing endpoint PCR assays, DG3, DG37, and DG72 (Table 1), were modified to two qPCR platforms, SYBR® Green and TaqMan® qPCR. Amplification of plasmid DNA dilutions showed that these qPCR assays have high reproducibility and resolution (Table 3).

TABLE 3

Standard curve performance parameters.

| Assay | Chemistry | Intercept | Slope | Efficiency[α] | $R^2$ | $Cq_{LOQ}$ | Resolution[β] | CV %[δ] |
|---|---|---|---|---|---|---|---|---|
| DG3 | SYBR | 33.962 | −3.485 | 0.936 | 0.994 | 30.624 | 0.140 | 1.728 |
| | TaqMan | 37.904 | −3.633 | 0.885 | 0.996 | 34.378 | 0.120 | 1.238 |
| DG37 | SYBR | 34.564 | −3.574 | 0.905 | 0.992 | 30.951 | 0.158 | 1.891 |
| | TaqMan | 38.150 | −3.604 | 0.894 | 0.995 | 34.522 | 0.128 | 1.324 |
| DG72 | SYBR | 35.543 | −3.545 | 0.915 | 0.988 | 32.062 | 0.192 | 2.210 |
| | TaqMan | 39.558 | −3.512 | 0.926 | 0.991 | 36.014 | 0.172 | 1.784 |

[α]Efficiency = $10^{(-1/Slope)} - 1$
[β]Resolution as estimated in Ruijter et al. 2013.
[δ]Mean CV % indicates percent coefficent of variation across all five dilutions for each assay.

The estimated marker $\log_{10}$ copies per ng of total DNA from the analysis of 244 fecal DNA extracts demonstrate a high abundance in dogs and extremely low in all other animal sources (Table 4).

TABLE 4

Estimated concentrations of canine-associated markers in target and non-target fecal sources

| | Marker concentrations per ng DNA | |
|---|---|---|
| | Mean | StdDev |
| DG3SYBR | 3.08 | 0.64 |
| DG3TaqMan | 3.14 | 0.73 |
| DG37SYBR | 2.09 | 0.53 |
| DG37TaqMan | 2.24 | 0.53 |
| DG72SYBR | 3.08 | 0.69 |
| DG72TaqMan | 3.47 | 0.64 |

Detection of Canine-Associated qPCR Genetic Markers in Stormwater Samples:

The prevalence of canine-associated markers among urban stormwater samples was low (Table 5). Quantifiable canine marker concentrations were between 15 and 115 copies per reaction. All three canine markers were found in the sample with the highest counts of *E. coli* and no markers were found in samples with fewer than 144 *E. coli* MPN/100 ml. Concentrations of molecular markers did not correlate with culturable bacteria counts (p>0.4). The detection of canine-associated markers in 5 out of 18 urban stormwater samples suggests that they persist long enough under environmental conditions to be useful for water quality applications, and that they are unlikely to be ubiquitous or native in the environment.

Although a few embodiments of the present invention have been shown and described, it would be appreciated by those skilled in the art that changes may be made in this embodiment without departing from the principles and spirit of the invention, the scope of which is defined in the claims and their equivalents.

SEQUENCE LISTING

>DogGFE_R2_1_F11_F_TQ_DG2_DG3
CCCTTCGTAATAGTTCCGCCACGAAGCAAGATTTCATTGTTTTCACC

TATTTTAGCCTCTACTCCCGGAAGCAAACGTCCCACGGCACCGATGC

GGAAATCATCTTTCCATTCACAAGACACCGTAGCCGTACTTTCTGTC

AATCCATAGCCGGCTACCATGTTAATACCTACCGAATGAACAAATTC

AGCCACCTTTCCAGGAATAGCCGCACCGGCAGTCGGGAAAAAGTTTC

CGTTGTCAATTCCTATCGTCTTTTTCAGGAGGCTGTAAATCGTCCGT

TCATAAAACTTATATTTCATATGCAACATCACGGGAGGAGTCTTACC

ATTCATCAGGTAATCAATGTTATGCGCCTTACCTACACGAAGGGCAT

CCAACATCAGACTCTTTTTCAGCCCCGTTGTTTCGTTAATCTTTTCC

AGTACGCCCGCGTAGACTTTTTCCCAGAAACGGGGCACACTGCACAT

GGCTGTAGGGCGAACCTCCTTGATGGTTTTCTGAATATCCTGCGGAC

GGAGGTTAATGCAGAGCAAACATCCACGGTCTAAACAATAATATGAC

CATGCCCGCTCAAAAATGGTA

>DogGFE_R2_5_B05_M13R_TQ_DG5
GGCACGTAGAGAATACGAAGGTGAGCGAGAGAACTGTTGCCAAGGAA

CTCGGCAAAATGGCCCCGTACGTTCGCAAGAAGGGGCGCTCGAGAGA

GCCGCAGTGAAAAGGCCCAAGCGACTGTTTAACTAAAACACAGCTCT

ATGCAAAGCCGTAAGGCGAAGTATATGGGGTGACACCTGCCCGGTGC

TABLE 5

Quantification and detection of canine-associated genetic markers in stormwater samples

| Sample | Total Coliforms[a] | E. coli | DG3 SYBR[β] | TaqMan | DG37 | SYBR | DG72 TaqMan | SYBR | TaqMan |
|---|---|---|---|---|---|---|---|---|---|
| 1 | 3.322 | 2.041 | – | – | – | – | – | – | – |
| 2 | 3.489 | 2.033 | – | – | – | – | – | – | – |
| 3 | 3.220 | 1.933 | – | – | – | – | – | – | – |
| 4 | 3.417 | 2.314 | 1.60 | 1.17 | – | – | – | 1.52 | 2.06 |
| 5 | 3.394 | 2.253 | – | – | – | – | – | – | – |
| 6 | 3.441 | 1.890 | – | – | – | – | – | – | – |
| 7 | 2.199 | 2.161 | + | – | – | – | – | – | – |
| 8 | 3.352 | 2.746 | – | – | – | – | – | – | – |
| 1 | 4.380 | 1.813 | – | – | – | – | – | – | – |
| 2 | 4.380 | 2.464 | – | – | – | – | – | – | – |
| 3 | 3.833 | 1.220 | – | – | – | – | – | – | – |
| 4 | 3.614 | 0.716 | – | – | – | – | – | – | – |
| 5 | 4.513 | 2.664 | – | – | – | – | – | – | – |
| 6 | 3.629 | 3.029 | – | – | – | – | – | + | – |
| 7 | 4.107 | 3.312 | – | – | – | – | – | – | – |
| 8 | 4.489 | 2.730 | – | – | – | – | – | – | – |
| 9 | 4.352 | 3.664 | 1.34 | – | – | + | – | 1.54 | 1.81 |
| 10 | 4.352 | 3.489 | + | – | – | – | – | – | – |

All quantities are $\log_{10}$ transformed. "+" indicates detection below the LOQ. "–" denotes below LOD.
[a]Total coliforms and *E. coli* MPN/100 ml were estimated using IDEXX-MPN methods.
[β]Units for marker concentration are copies/reaction

```
TGGAAGGTTAAGGGGATCTGTTCGTCGCAAGACAAAGCAGTGGTCCG

AAGCCCCAGTGAACGGCGGCCGTAACTATAACGGTCCTAAGGTAGCG

AAATTCCTTGTCGGGTAAGTTCCGACCCGCACGAAAGGCGTAATGAT

TTGAGCGCTGTCTCGACAATCCAGTG

>DogGFE_R2_2_E09_M13R_TQ_DG29
TGAAATAAGAACCAGGGAAAACCTTGAGGAAAGGAGCTATCATAGC

TGACGCATATCAGGAACACTGATACCGTTCACGCCCAGTCTGCGCTT

CCTTTGAGCCTGTAGTCTCAAAGGCGCTCGACGGATTCGCGTAAACG

GTGTCAATGTCCCGGATATGCTGTTGGCATGATAGCTCTTTGTGTAT

AGGTGTGCAGATGGAGAGTGTGTTTGAATAAATCGAAAAGTGGAGG

CGGATTATGGAAGAGTGTATGACAAAGAGGGGAGCCAGGCTGATTGT

GTATGTGCCTAAGGAGCTGGATCATCATTTTGCAGGGGAGATGACAG

AGATGGTGGATAAGGAGCTTAAGAAGGGCTGTATTAAACAGCTTGTC

TTTGATTTTTCTAAGACAACGTTTATGGACAGTTCTGGCATTGGGAT

GCTAATGGGAGAAAGCGGCTGTTAAGCTACAGCGGAGGAACCGTAA

GTGCTATTCATGTTAATGACCGGATTTTGCGGATTATGCAGCCTTCG

GGCATCTGGAAACACATGGAAATCAGCCAGGAA

>DogGFE_R2_6_E05_M13F_TQ_DG37
TAGTCCTTTTCTCCCACGGTCATCTGCTCTTTCATACTGTCCATAAG

AAGCTGCTTACATTCCTGTGGATCCTTAATATGCTTTTCTGCCACCT

GCTCCTTTAAACGTTCAATAATAGAAGTGGTAGTATTAATTCCAATG

TCGCCCATAACCAAGATTTCTTCGATTTCCTCATAGAAATCCTCGTC

AATACTGGAATAACCGCTAAAAATAGAATCAATTCCTGATACAATGT

TTTCTCTGGTTTTTGAAAGACCCTCTACCAATCTTTTAAAAAAACCT

TTTTTCTCTTTTCCCTCTGCCATAGTTCCTCCTATTTATCTAAATCA

TGCTCAATGAGTTTTACAGACACCAGGGTAGACACACCTTTTTCCTG

CATGGTAATTCCATAGAGCCTGTCTGCTGCTGTCATGGTT

>DogGFE_R2_3_B06_M13F_TQ_DG39
GTGCTGACCAAGGAGGTGAGAAGCAGCACTATCAAGGCAATTTTAAG

AATCAGCTTGCGCCGATTGATTATGTCAGATGGATGAAGCATAGTGA

CTGTGTAACTTAAATGGGTGTTCAGAATTCACACATTTGAACACTTG

CTTGGGTAACTTGAACTTTAAACTCGATGCTTAAAACGCCTGAATGG

TGTAAAGGTAAAGAACGGCTGCGGGAATGGCAAGCAGTGAGGAGTCG

AAGCGGTCGAGCATGCCGCCGTGGCCGGGGAGCACATGGCCGCTGTC

TTTAATACCCAGCTGACGCTTGAAAAGGCTTTCGACCAGGTCGCCCC

AGGTGCCGAATACGCATACCGTCAGGCCCAGACCCAACCAGTGGAGA

AGGGGCAAGGTG

>DogGFE_R2_3_F12_M13F_TQ_DG46
GACAATGCCGACAGGATAGCCATTGGCATAAACGGGATTCGACACTG

AAAGACCTACAACGTTCTTGAACTTTACGTAATAGGTATTAGTGGAT

TGAAAAACATTGATACCCTTGAGGAAATTGAGTCCTATAAACAGCAG

CACAAGGGCTACTACAGCGGTAAGGGCAATTTTAATTTCTTTCTTCA

TTGTATGGTGAATGAGGTTGTACTTAAAGGATTGGGATGCCCATGAT

ATGGGGGAGTGGTGGCGCAGAAGCGTAGGGCTTACTTGCGTTCGGC

TGCACGGGCTTGCTTAATGGTTACTTTCTGACCATTGAGAAAGGCTA

CCATATAGGCATCGGGGAGTTTCTTCAACACTCCGGGCATGGCGCGA

TGTGCTTCGGCATAGTTCGTGAACGAACCGTGATAGTATTTATAGAG

GTTGCCTTCTTTCACTCGCTTTACGGTGAGTCCCTTGAACTGGGGGT

CGCGGGGCGAAATTTCGCGAGTTCCGGCTGCCAGTTGAATGCAGTAG

GTTACGACATTGCCGACCACGGTA

>DogGFE_R3_8_C01_M13F_TQ_DG68
CGGTGAGCTGATTGGTACAGGATTTGACCGAAACTATGAAGGTCTTA

CCGGAGATATCGCCTACAATCCGCAGCTACAGCGTGCTGCTTGTGTA

GACATCCGCTACACATTGTTTATCATTGATAAATTCGCAGGTGCACG

CCATCTCATCGATGAAATGACAATCATCCGATAAGGTTGATTTTACC

ATAAAAAAAGACATCCTACCTGATTACCCGACATAAGTCTGGGGTT

TATCAAAGTAGGATGTCTTTTTTTATACTATCCTGTAAAAAGAAA

AAGATTATTTGCTTAATGCTTGAATCGTATGACGCACACGTTCTGCA

GTAGTTACGGGATATACATATTCATCTTGGTCTGAACTGCCCAGGGT

A

>DogGFE_R3_7_B02_M13F_TQ_DG72
TATCTATCCGCCATAAAGATGCATTTGGCGCAGGAGGAAGTACCAGC

GGTGGTGTAGATATACGCCCTTTCCCAAACAACTGGGAGATGAAAAA

GCAACTTGGTGAGGAAAAGGAGAATCAAACCCGCTGGGACAATCATA

CAGTAATGACTCAACTTGACAAAATCAATCCGGGTGATTGGCTTTA

ATCATAGATTGCGGTTCAGAGGATTTCTTTCTCGAAGTAAACGAGCA

GCTGCATAAGGTTCTGAGTGACAAAGGTATTCCGCATGACTTCATCA

TCCGCCCGGGAGTACACGACGGGAAATACTGGAATAACTCGATTGAT

TACCAATGGATGTTTTTCAAGAAGTTCTTCGATGGATACCGCAATAA

TCAAGACATACGCCCGTAGGTAAAGGCATCTCTCCCCAACCAAGGTG

CCGATAAAGGGATATACAGCTTAAATACATAGGTAAACTTGCCAAGA

AGAAGGTATTGATTATTTCAAGGCTTTTTGTAAATTTGCAATTATAT

ACTCAGAAAAGAACGATAATATGGAAATAACCAGTGCTGAATTTGT

AGTAAGTAACTCGCGTGCCGACATGTGCCCGGACACCCACCTTCCCG

AACATGCCTTTATCGGACGCTCGAACGTAGGAGAATCCAGCTTAATC

AATATGCTGACCAATCACTCCAATTTGGCCATGACCTCCTCAACCCC

GGTA

>DogGFE_R2_4_G07_M13F_TQ_DG74
CACGGTAAAAAACGGACTGACTCCCTTCGCTTCACTGATTTCAGCAA

GTGGAATATCATGTGTAATAATAGAAGGGAAGAAAGCTTCGCCTACC
```

SEQUENCE LISTING

CCGTAAGAAAGAAAACCTGAAAACAGCGTTGCTCCATAAGCCAACAA

AGCGGTTACTGCCAACATCTTTCCGGCTCCTTTACCTATATCGGCAA

TGGCTGGGGTAACTAATCCGACTATAATCAGCGGAATGATAAAATTA

AGGAACTGACTGAACAACCCGTTGAAGGTGACAAAAAGGCGTACCCG

GTG

>DogGFE_R2_5_D09_M13F_TQ_DG75
TTGAGCTTCTTCCAGTTAGACGACCCTGTGCTTTGTCAGATTCGTGA

TGAAATCTTGAATTTGGATGTGAATAATCTGACTCCTCTGGAGGCAC

TGAATAAGTTGAATGATATTAAGCGGATTGTAAGGGGAAAGTAGACT

TATAAATCATAAACTTAAAAACGAAAGCCCTATGAAAACAATGAAGT

TAGGACTTCTTCCTCCCATTCTTATTACGATAGTTTTAGGTATTTTT

GCCGGGATGGTTTCACCAGCTTTCCCGGTACGCCTTTTTGTCACCTT

CAACGGGTTGTTCAGTCAGTTCCTTAATTTTATCATTCCGCTGATTA

TAGTCGGATTAGTTACCCCAGCCATTGCCGATATAGGTAAAGGAGCC

GGAAAGATGTTGGCAGTAACCGCTTTGTTGGCTTATGGAGCAACGCT

GTTTTCAGGTTTTCTTTCTTACGGGGTAGGCGAAGCTTTCTTCCCTT

CTATTATTACACATGATATTCCACTTGCTGAAATCAGTGAAGCGAAG

GGAGTCAGTCCGTTTTTTACCGTGACTATTCCTGAGCCCCTGAATGT

GATAACATGGCA

>DogGFE_R3_7_H11_M13F_TQ_DG80
GAACGACCCTTCGCGTCCGTGTCATAAAACCTACACCATCGACATGG

ACCGTCACTCGTACGATGGCCAGCAATGGACTTACCTGAACCTGCCG

ATGGAGGAAATCAAGCAGATGGCCATTGCCTCGATTAAGGACTCAAC

GATGATGTACTACTCATGCGACGTGGGCAAATTCCTGAACGGCAAAA

CGGGTATTCTTTCGTTGCAGAACTACGACTACGAGTCGCTTTTCGGC

ACCAACTTCCCCATGACGAAGGCTGAACGCATCAGCACCTTTGCATC

GGCGTCGAGCCATGCCATGACGCTGATGGCCGTAGACCTCGACGCCA

ACGGCAAACCGACGAAGTGGATGGTTGAAAACTCTTGGGGTGCTACT

TCGGGCCACAACGGTA

---

What is claimed is:

1. A method for detecting dog-fecal contamination in a water sample, comprising the steps of:

1) contacting the sample of water to a sequence containing at least one nucleic acid-sequence chosen from SEQ ID NO: 1, 2, 3, 4, 5, 6, 7, 8, 9, 10, or 11, or sequences fully complementary thereto, and 2) subjecting the product of step 1 to a test for binding of material in the water sample to the sequences listed in step 1, wherein binding or sequences identified in step 1) is deemed evidence of dog-fecal contamination in the sample.

2. The method of claim 1, wherein the fecal contamination is a fecal bacteria.

3. The method of claim 2, wherein the fecal bacteria is a *Bacteroides* spp.

4. The method of claim 1, wherein binding is detected by an amplification reaction.

5. The method of claim 4, wherein the amplification reaction is polymerase chain reaction (PCR), qPCR, or digital PCR.

* * * * *